(12) United States Patent
Jimenez

(10) Patent No.: US 9,277,931 B2
(45) Date of Patent: Mar. 8, 2016

(54) ORAL CARE IMPLEMENT

(75) Inventor: Eduardo J. Jimenez, Manalapan, NJ (US)

(73) Assignee: COLGATE-PALMOLIVE COMPANY, New York, NY (US)

( * ) Notice: Subject to any disclaimer, the term of this patent is extended or adjusted under 35 U.S.C. 154(b) by 287 days.

(21) Appl. No.: 13/992,151

(22) PCT Filed: Dec. 13, 2010

(86) PCT No.: PCT/US2010/060105
§ 371 (c)(1),
(2), (4) Date: Jun. 6, 2013

(87) PCT Pub. No.: WO2012/082102
PCT Pub. Date: Jun. 21, 2012

(65) Prior Publication Data
US 2013/0274774 A1    Oct. 17, 2013

(51) Int. Cl.
A61B 17/24    (2006.01)

(52) U.S. Cl.
CPC .................................. *A61B 17/244* (2013.01)

(58) Field of Classification Search
CPC ........... A61B 17/246; A61B 2017/242; A61B 13/00; A61B 17/24; A61B 17/244
See application file for complete search history.

(56) References Cited

U.S. PATENT DOCUMENTS

| | | | |
|---|---|---|---|
| 3,683,924 A | 8/1972 | Louie | |
| 4,582,059 A | 4/1986 | Tiwari | |
| 5,217,475 A | 6/1993 | Kuber | |
| 5,569,278 A | 10/1996 | Persad | |
| 5,709,004 A | 1/1998 | Paduano et al. | |
| 5,827,308 A | 10/1998 | Thakur et al. | |
| 5,893,860 A | 4/1999 | Ripich et al. | |
| 5,916,228 A | 6/1999 | Ripich et al. | |
| 6,056,763 A | 5/2000 | Parsons | |
| 6,363,949 B1 | 4/2002 | Brown | |
| 6,440,149 B1 | 8/2002 | Potti | |
| 6,475,172 B1 | 11/2002 | Hall | |
| 6,647,581 B1 | 11/2003 | Persad et al. | |
| 7,029,484 B2 | 4/2006 | R | |
| 2006/0052805 A1* | 3/2006 | Cwik | 606/161 |
| 2006/0058821 A1 | 3/2006 | Jansheski | |
| 2004/0092981 A1 | 5/2004 | Barlow et al. | |

FOREIGN PATENT DOCUMENTS

| | | |
|---|---|---|
| RU | 2181988 | 5/2002 |
| WO | WO 98/09572 | 3/1998 |
| WO | WO 98/09573 | 3/1998 |

OTHER PUBLICATIONS

International Search Report and the Written Opinion of the International Searching Authority issued in International Application PCT/US2010/060105 mailed Aug. 30, 2011.

* cited by examiner

*Primary Examiner* — Jonathan W Miles

(57) ABSTRACT

An oral care implement for cleaning a user's tongue and/or soft tissue surfaces. In one aspect, the invention can be an oral care implement comprising: a handle extending along a longitudinal axis; first and second prong members extending from a distal end of the handle, each of the first and second prong members diverging from the longitudinal axis and having a distal end; a blade for scraping soft tissue, the blade extending between the distal ends of the first and second prong members; and the blade integrally formed with the first and second prong members, the first and second prong members transitioning into the blade at the distal ends of the first and second prong members.

19 Claims, 4 Drawing Sheets

ORAL CARE IMPLEMENT

CROSS-REFERENCE OF RELATED APPLICATIONS

This application is a U.S. national stage entry under 35 U.S.C. §371 of Patent Cooperation Treaty Patent Application No. PCT/US2010/060105, filed Dec. 13, 2010, the entirety of which is incorporated herein by reference.

FIELD OF THE INVENTION

The present invention relates generally to the field of oral care, and specifically to an apparatus for cleaning oral soft tissue, such as the tongue.

BACKGROUND OF THE INVENTION

According to the American Dental Association, a major source of bad breath in healthy people is microbial deposits on the tongue, where a bacterial coating harbors organisms and debris that contribute to bad breath. The tongue is a haven for the growth of microorganisms since the papillary nature of the tongue surface creates a unique ecological site that provides an extremely large surface area, favoring the accumulation of oral bacteria. Anaerobic flora and bacteria residing on the tongue play an important role in the development of chronic bad breath commonly called halitosis. In general, the bacteria produce volatile sulfur compounds (VSC). If there is enough buildup of the sulfur compounds, the result can be bad breath or oral malodor.

While bladed tongue scrapers have been used in the past in order to remove bacteria from the tongue, these scrapers are inadequate in respect to their effectiveness on the soft tissue surface of the tongue. Broad flat scraping blades are limited in their ability to reach between the papillae where the bacteria and microdebris have collected. Moreover, notwithstanding the benefits to be gained by any ability to clean the tongue, some users avoid the use of such blades because of lack of comfort on the tongue surface.

In addition to bladed tongue scrapers, toothbrushes have been developed that have a tissue cleanser on the toothbrush head. However, these oral care implements are limited in that the tissue cleanser is provided only on one major surface of the head and tend to be small in size and can be ineffective in scraping debris off of the tongue.

Furthermore, known tongue scrapers and soft tissue cleansers have a predetermined width. Thus, for persons with small mouths, such as children, these known devices are inefficient or uncomfortable to use. While a tongue scraper having an adjustable width is know, such adjustable width tongue scrapers are both cumbersome and complicated in their manufacture and use, thereby resulting in the devices being expensive to manufacture and/or undesirable to use.

Hence, there is a need for an apparatus for cleaning soft tissue within a user's mouth that provides effective removal of bacteria and other debris while maintaining comfort to the user. There is also a need for an apparatus for cleaning soft tissue within a user's mouth in which a size of the portion of the apparatus that contacts the user's soft tissue is adjustable. There is a further need for an apparatus for cleaning soft tissue within a user's mouth which is easy to manufacture and has user-friendly design.

BRIEF SUMMARY OF THE INVENTION

The present invention is directed to an oral care implement for cleaning a user's soft oral tissue, such as the tongue.

In one embodiment, the invention can be an oral care implement comprising: a handle extending along a longitudinal axis; first and second prong members extending from a distal end of the handle, each of the first and second prong members diverging from the longitudinal axis and having a distal end; a blade for scraping soft tissue, the blade extending between the distal ends of the first and second prong members; and the blade integrally formed with the first and second prong members, the first and second prong members transitioning into the blade at the distal ends of the first and second prong members.

In another aspect, the invention can be an oral care implement comprising: a handle extending along a longitudinal axis; first and second prong members extending from a distal end of the handle, each of the first and second prong members having a distal end; a blade for scraping soft tissue, the blade connected to and extending between the distal ends of the first and second prong members; and wherein the blade comprises a base formed of a first material and a layer formed of a second material overlying at least a portion of the base, the first material having a hardness that is greater than a hardness of the second material.

In yet another aspect, the invention can be an oral care implement comprising: a handle extending along a longitudinal axis; first and second prong members extending from a distal end of the handle, each of the first and second prong members having a distal end; a blade for scraping soft tissue, the blade extending between the distal ends of the first and second prong members; and wherein the handle, the first and second prong members and the blade are integrally formed, the handle transitioning into the first and second prong members at the distal end of the handle and the first and second prong members transitioning into the flexible blade at the distal ends of the first and second prong members.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE INVENTION

Figure 1:
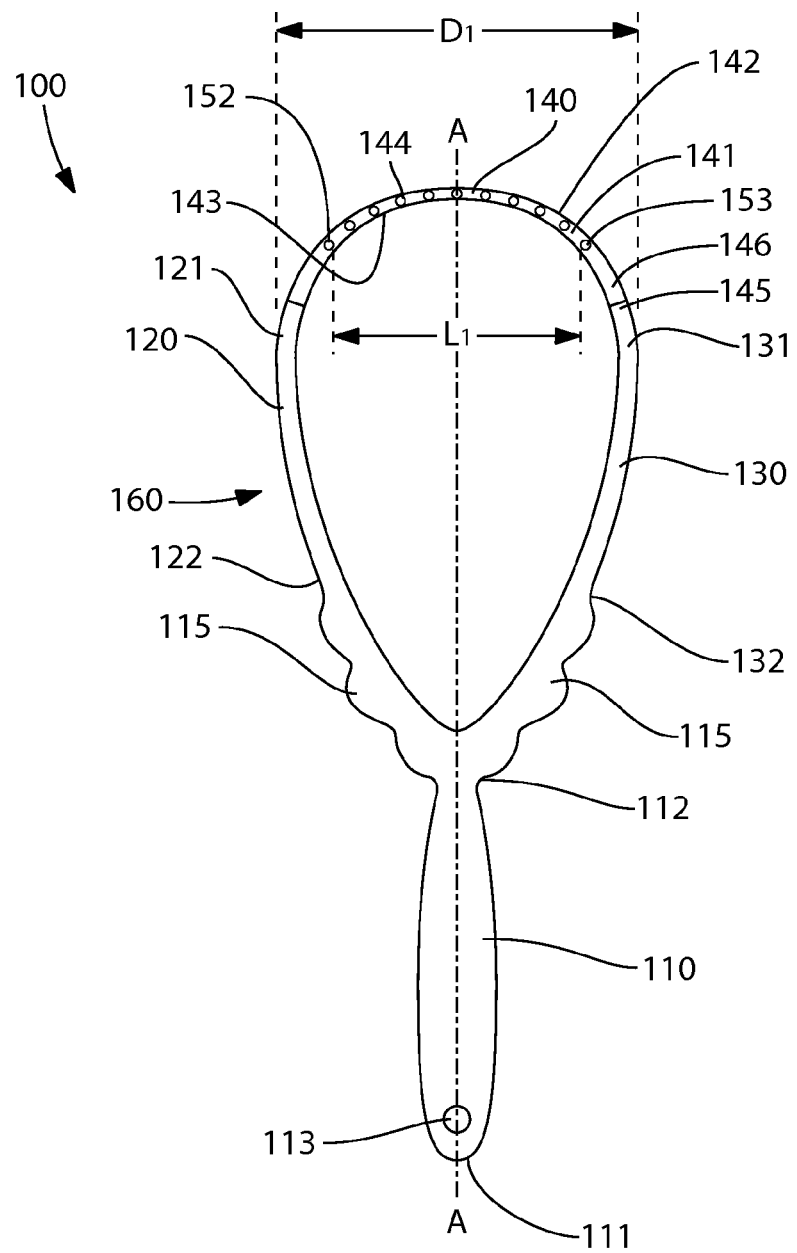
FIG. 1 is a front view of a tongue scraper in a normal state in accordance with one embodiment of the present invention.

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of the exemplary embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "left," "right," "top," "bottom," "front" and "rear" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," "secured" and similar refer to a relationship wherein structures are secured or attached to one another either directly or indirectly through intervening structures, as well as both movable or rigid attachments or relationships, unless expressly described otherwise. Moreover, the features and benefits of the invention are described by reference to the exemplary embodiments illustrated herein. Accordingly, the invention expressly should not be limited to such exemplary embodiments, even if indicated as being preferred. The discussion herein describes and illustrates some possible non-limiting combinations of features that may exist alone or in other combinations of features. The scope of the invention is defined by the claims appended hereto.

Referring to FIG. 1, an oral care implement 100 is illustrated according to one embodiment of the present invention. The oral care implement 100 generally comprises a handle 110 and a head portion 160. The head portion 160 comprises a first prong member 120, a second prong member 130 and a blade 140. For purposes of discussion, the prong members 120, 130 will be conceptually discussed as being separate components from the blade 140. However, as discussed in greater detail below, the prong members 120, 130 and the blade 140 are integrally formed as a unitary structure in the exemplified embodiment of the present invention. Of course, the invention is not so limited in all embodiments.

The handle 110 provides a user with a mechanism by which he/she can readily grip and manipulate the oral care implement 100. The handle 110 includes ergonomic features which provide a high degree of control for the user while maintaining comfort. For example, the handle 110 can include contoured outer surfaces forming finger depression regions. Further, the handle 110 can include an elastomeric overlay if desired.

The handle 110 extends from a proximal end 111 to a distal end 112 along a longitudinal axis A-A. The handle 110 comprises an aperture 113 at its proximal end 111 to enable the oral care implement 100 to be hung from a hook, nail, pin or other structure that is commonly used in a bathroom or elsewhere to hang oral care appliances. Of course, in certain embodiments, the aperture 113 may be omitted from the handle 110 if desired.

The first and second prong members 120, 130 extend from the distal end 112 of the handle 110 in a forked-manner. More specifically, the first and second prong members 120, 130 extend from the distal end 112 of the handle 110 in a forked-manner such that the first and second prong members 120, 130 diverge from the longitudinal axis A-A with distance from the distal end 112 of the handle 110. As a result, the further the distance from the distal end 112 of the handle 110, the larger the transverse distance between the first and second prong members 120, 130. While the first and second prong members 120, 130 diverge from the longitudinal axis A-A along their entire length in the exemplified embodiment, in certain other embodiments, the first and second prong members 120, 130 may diverge from the longitudinal axis A-A only for a portion of their length. In such embodiments, the first and second prong members 120, 130 may diverge from the longitudinal axis A-A for only a portion of their length from the distal end 112 of the handle 110 and then: (1) straighten out and continue in a substantially parallel manner for their remainder; and/or (2) begin to converge toward the longitudinal axis A-A for their remainder.

The first prong member 120 has a distal end 121 and an outer surface 122 and the second prong member 130 has a distal end 131 and an outer surface 132. As will be better understood from the description below, in the exemplified embodiment, the distal ends 121, 131 of the first and second prong members 120, 130 are conceptual in nature as the prong members 120, 130 and the blade 140 can be integrally formed as a unitary structure. In other words, the first and second prong members 120, 130 transition directly into the blade 140 to form the unitary structure of the head portion 160. Thus, in certain embodiments, the first and second prong members 120, 130 do not actually terminate at the distal ends 121, 131. For purposes of certain embodiment, the distal ends 121, 131 of the first and second prong members 120, 130 are those sections where the first and second prong members 120, 130 transition into the blade 140.

In the exemplified embodiment, the blade 140 extends between the distal ends 121, 131 of the first and second prong members 120, 130 in a contoured manner. During use of the oral care implement 100, the blade 140 scraped across the desired oral soft tissue, such as the tongue. In the exemplified embedment, the blade 140 is integrally formed with the first and second prong members 120, 130 and transitions directly from the distal ends 121, 131 of the first and second prong members 120, 130.

The head portion 160 can be integrally formed using a molding, milling, machining or other suitable process. In other embodiments, the first and second prong members 120, 130 and the blade 140 may be formed as separate components which are operably connected at a later stage of the manufacturing process by any suitable technique known in the art, including without limitation thermal welding, a tight-fit assembly, a coupling sleeve, adhesion, fasteners or the like. Whether the first and second prong members 120, 130 and the blade 140 are of a unitary or multi-piece construction (including connection techniques) is not limiting of the present invention unless specifically stated in the claims.

In certain embodiments, the handle 110 is also integrally formed as a single unitary structure with the first and second prong members 120, 130. In such embodiments, the entirety of the oral care implement 100 is an integrally formed unitary structure. Of course, elastomeric overlays, covers and/or other components may be applied to the unitary structure if desired. The oral care implement 100, when a single unitary structure, can be formed using, without limitation, any of the processes discussed above. Of course, the invention is not so limited in all embodiments, and the handle 110 and the prong members 120, 130 may be separately formed and later connected in the manner discussed above.

In one embodiment, the handle 110, the first and second prong members 120, 130, and the blade 140 are formed of a hard, yet flexible material, such as a bendable plastic material. In one embodiment, the handle 110, the first and second prong members 120, 130, and the blade 140 are formed of a polypropylene. Of course, the invention is not so limited and the handle 110, the first and second prong members 120, 130, and the blade 140 may be foamed of other suitable materials as would be known to persons skilled in the art. Moreover, even when the handle 110, the first and second prong members 120, 130, and the blade 140 are formed of the same material, the flexibility of each component can be varied as desired by adjusting the cross-sectional size and/or shape as desired.

As mentioned above, improved gripping of the handle 110 and the first and second prong members 120, 130 may be facilitated by covering a portion of the flexible plastic material with a second material, such as, for example, a thermoplastic elastomer. Constructing the handle 110 and the first and second prong members 120, 130 out of a hard, flexible plastic covered with an elastomer provides for easy flexing and squeezing by the user as will be discussed in more detail below with reference to FIG. 4.

The prong members 120, 130 are provided with finger grip protrusions 115. The finger grip protrusions 115 are a series of contours formed on the outer surfaces 122, 132 of the first and second prong members 120, 130 that are designed to comfortably fit the fingers of a user therebetween. The finger grip protrusions 115 may be formed directly into the material used to form the prong members 120, 130 or may be formed from an elastomeric overlay or other covering as described above. Of course, in certain embodiments the finger grip protrusions 115 may be omitted altogether.

The blade 140 is an elongated flat strip of material extending between the first prong member 120 to the second prong member 130. The blade 140 has a first edge 141, a second edge 151 (FIG. 2), a first major surface 142 and a second major surface 143. The first edge 141 of the blade 140 is used to engage a user's soft oral tissue during use of the oral care implement 100. In some embodiments, the second edge 151 of the blade 140 can also used to engage the user's soft tissue surfaces (i.e., scraping the tongue). In such an embodiment, the second edge 151 can be designed to include any and/or all of the feature described below for the first edge 141 in addition to and/or instead of the first edge 141.

A plurality of protuberances 144 protrude from the first edge 141 of the blade 140. The plurality of protuberances 144 are intended to engage the soft oral tissue of a user's mouth in order to provide an effective and efficient cleaning of those surfaces by reaching deeper into papillae and/or small crevices. Specifically, when the first edge 141 of the blade 140 is engaged or otherwise pulled against or across the soft oral tissue, the protuberances 144 provide for gentle engagement with the soft tissue while reaching downward into the recesses of adjacent papillae of the tongue for removal of debris and bacteria.

Figure 2:
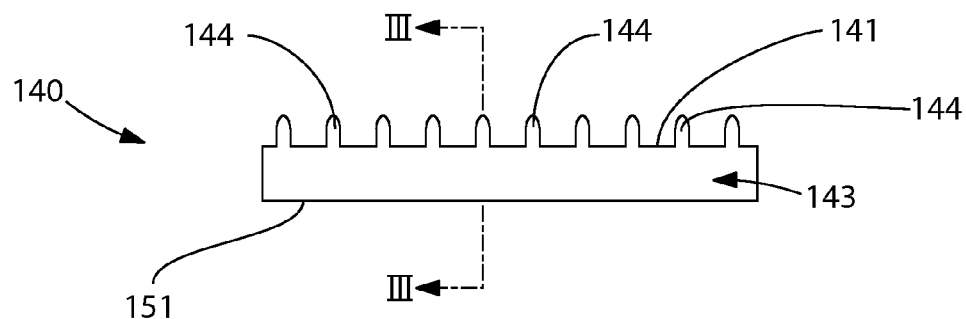
FIG. 2 is a side view of the blade of the tongue scraper of FIG. 1 in an unfolded state, in accordance with one embodiment of the present invention.

Referring now to FIG. 2, the blade 140 and its protuberances 144 will be described in greater detail. In FIG. 2, the blade 140 is illustrated in an unbent state and detached from the oral care implement 100. Of course, when the blade 140 is attached to (i.e., or integrally formed with) the first and second prong members 120, 130, the blade 140 is curved so that the bottom major surface 143 of the blade 140 is concave while the top major surface 142 of the blade 140 is convex.

In some embodiments, the plurality of protuberances 144 are formed as nubs. As used herein, the term "nub" is generally meant to include a column-like protrusion (without limitation to the cross-sectional shape of the protrusion) which is upstanding from a base surface, such as the first edge 141 of the oral care implement 100. In a general sense, the nub, in one construction, has a height that is greater than the width at the base of the nub (as measured in the longest direction). Nevertheless, nubs could include projections wherein the widths and heights are roughly the same or wherein the heights are somewhat smaller than the base widths. Moreover, in some circumstances (e.g., where the nub tapers to a tip as illustrated in FIG. 2 or where the nub includes a base portion that narrows to a smaller projection), the base width can be substantially larger than the height. Of course, the protuberances 144 are not limited to column-like or cylindrical nubs, and the protuberances 144 can take on a wide variety of shapes and structures, including conical, rod-like, hemispherical, irregular or the like.

The protuberances 144 protrude outward from the first edge 141 of the blade 140 in order to engage a user's soft oral tissue when the first edge 141 of the blade 140 is scraped across the desired soft tissue. Although the blade 140 in FIG. 2 is illustrated as having ten protuberances 144 equally spaced across the length of the blade 140, more or less protuberances may be used in other embodiments as desired. The invention is in no way limited by the number and/or arrangement of the protuberances 144 on the first edge 141 of the blade 140 unless specifically recited.

Referring now to FIGS. 3a-3d, a number of embodiments of the construction of the blade 140 will be described. The blade 140 comprises a base 145 formed of a first material and an outer layer 146 formed of a second material. In embodiments where the blade 140 is integrally formed with the first and second prong members 120, 130, the base 145 is the portion of the blade 140 that is integrally formed with the first and second prong members 120, 130. The outer layer 146, on the other hand, does not extend over and cover the first and second prong members 120, 130 in the exemplified embodiment. However, such an arrangement is possible in other embodiments. The outer layer 146 overlies at least a portion of the base 145 to provide comfort and efficient cleaning of the soft tissue surfaces. Thus, the base 145 is preferably formed of the same material as the first and second prong members 120, 130 as discussed above. However, due its strip-like shape, the blade 140 can flex easily under pressure exerted thereon by the first and second prong members 120, 130.

The first material, which forms the base 145, has a hardness value that is greater than a hardness value of the second material, which forms the outer layer 146. In one embodiment, the first material has a hardness value in a range of 80 to 100 Shore A and the second material has a hardness value of approximately 30 to 50 Shore A. In one more specific embodiment, the material has a hardness value of approximately 90 Shore A and the second material has a hardness value of approximately 40 Shore A. In some embodiments, the base 145 is constructed of thermoplastic material, such as, for example, polypropylene and the layer 146 is formed of an elastomeric material such as, for example, a thermoplastic elastomer. Of course, the invention is not so limited and other suitable materials may be used for the base 145 and the outer layer 146 as would be known to persons skilled in the art.

The plurality of protuberances 144 are integrally formed with the outer layer 146 and, thus, are formed of the same material as the outer layer 146. Thus, the protuberances 144 are soft and flexible when the outer layer 146 is formed of a soft thermoplastic elastomer. However, in other embodiments, the protuberances 144 can be formed integrally with the base 145 and, thus, be formed of the same material as the base 145. In such an embodiment, the outer layer 146 may be omitted or, as illustrated in FIG. 3f, protuberances 144 may protrude through the outer layer 146 so that only a tip portion of the protuberances 144 extend therefrom.

In the exemplified embodiment, the outer layer 146 forms the first edge 141 of the blade 140. Thus, the protuberances 144 contact a user's soft oral tissue when the oral care implement 100 is used. The soft, flexible material of the layer 146 (and protuberances 144) enables the first edge 141 of the blade 140 to more closely follow the natural contours of the oral tissue surfaces, such as the tongue, cheeks, lips, and gums of a user. Moreover, the soft, flexible material of the protuberances 144 enables the protuberances 144 to flex as needed to penetrate and clean the soft oral tissue in the mouth. Thus, the first edge 141 of the blade 140 and the protuberances 144 work in a concerted manner to penetrate adjacent papillae of the tongue and scrape bacteria out of a user's oral cavity.

Figure 3A:
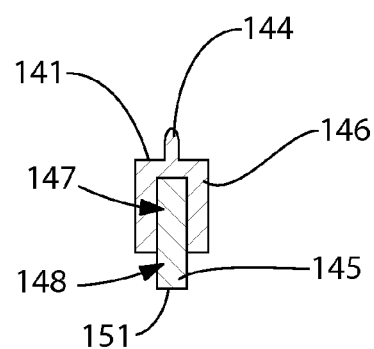
FIG. 3a is a cross-sectional view of the blade taken along the line of FIG. 2.

Referring to FIG. 3a, the details of a first embodiment of the blade 140 having a base 145 and an outer layer 146 will be described. In this exemplified embodiment, the outer layer 146 only overlies a first portion 147 of the base 145 while leaving a second portion 148 of the base uncovered. This enables the benefits of using the layer 146 to be achieved while reducing costs by not full encasing the base 145 within the material of the layer 146. Furthermore, by not fully encasing the base 145 within the material of the layer 146, the second edge 151 remains of the blade 140 exposed (i.e., uncovered by the outer layer 126) so that it is comprised of only the harder first material. In such an embodiment, the user may scrape the first edge 141 of the blade 140 across the tongue first to enable the protuberances 144 to remove bacteria from the papillae and, in a second motion, the user may scrape the second edge 151 of the blade 140 across the tongue to pull the removed bacteria forward and out of the mouth.

Figure 3B:
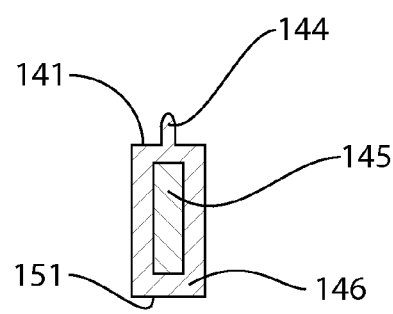
FIG. 3b is a cross-sectional view of a blade in accordance with a second embodiment of the present invention that can used with the tongue scraper of FIG. 1.

Referring to FIG. 3b, the details of a second embodiment of the blade 140 having a base 145 and an outer layer 146 will be described. In this embodiment, the layer 146 completely surrounds the base 145. In this embodiment, comfort of using the oral care implement 100 is enhanced by ensuring that only the soft material of the layer 146 will engage the user's soft tissue, irrespective of whether the first and/or second edges 141, 151 are used to scrape the soft tissue. By surrounding the base 145 with the material of the outer layer 146, the user may first scrape the first edge 141 of the blade 140 across the tongue in order to enable the protuberances 144 to remove bacteria from the papillae. The user may then scrape the second edge 151 of the blade 140, which is devoid of protuberances 144, across the tongue to pull the removed bacteria forward and out of the mouth. In this embodiment, the second edge 151 is formed from the soft, flexible material of the layer 146 for an added sense of comfort to the user and to enable the second edge 151 of the blade 140 to flex and conform to the contours of the tongue and/or soft tissue surfaces.

Figure 3C:
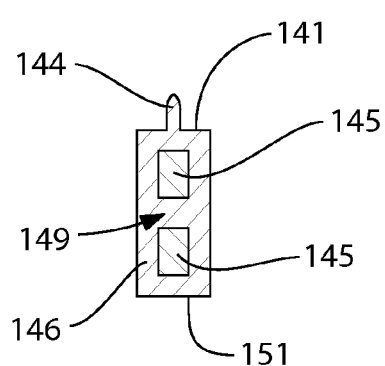
FIG. 3c is a cross-sectional view of a blade in accordance with a third embodiment of the present invention that can used with the tongue scraper of FIG. 1.

Referring to FIG. 3c, the details of a third embodiment of the blade 140 having a base 145 and an outer layer 146 will be described. In this embodiment, the base 145 is constructed with one or more apertures 149. The layer 146 surrounds the base 145 and extends through the aperture 149. The use of the apertures 149 facilitates a more secure attachment of the outer layer 146 to the base 145.

Figure 3D:
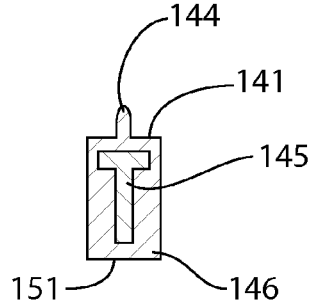
FIG. 3d is a cross-sectional view of a blade in accordance with a fourth embodiment of the present invention that can used with the tongue scraper of FIG. 1.

Referring to FIG. 3d, the details of a fourth embodiment of the blade 140 having a base 145 and an outer layer 146 will be described. In this embodiment, the base 145 has a T-shaped cross-section and the layer 146 substantially surrounds the base 145. The T-shaped cross-section of the base 145 also enhances the attachment of the layer 146 to the base 145 as described above with reference to FIG. 3c.

It should be understood that although only four embodiments of the blade 140 having the base 145 and outer layer 146 are described above, other combinations of a first material and a second material may be used to form the blade 140 as would be known to persons skilled in the art. For example, in some embodiments the layer 146 may be omitted altogether and the protuberances 144 can be formed of the same material as the base 145. Furthermore, in other embodiments the first edge 141 comprising the protuberances 144 can be formed of the harder material of the base 145 and the outer layer 146 could overlie the base 145 in a manner so as to cover (and form) only the second edge 151 of the blade 140.

Figure 3E:
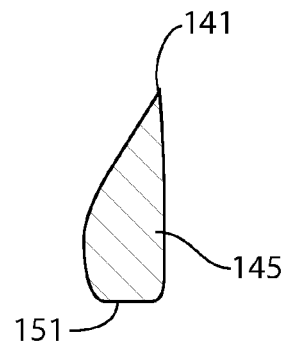
FIG. 3e is a cross-sectional view of a blade in accordance with a fifth embodiment of the present invention that can be used with the tongue scraper of FIG. 1.
Figure 3F:
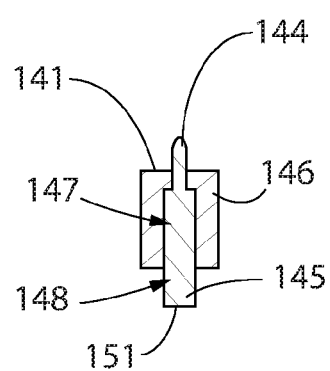
FIG. 3f is a cross-sectional view of a blade in accordance with a sixth embodiment of the present invention that can be used with the tongue scraper of FIG. 1.

Referring now to FIG. 3e, the details of a blade 140 formed of only the material of the base 145 will be described. In this embodiment, the blade 140 does not have any protuberances 144 protruding from the first edge 141 of the blade 140. Furthermore, in this embodiment, the blade 140 is only formed of the first harder material as a unitary part of the first and second prong members 120, 130. In certain embodiments, the blade 140 may taper towards the first edge 141 to provide a first edge 141 that terminates in an apex for engaging and scraping a user's soft tissue and/or tongue surfaces. The apex may be rounded in certain embodiments to avoid cutting. In other embodiment, the apex may be overlaid with the softer material. Furthermore, in the exemplified embodiment, the second edge 151 of the blade 140 may be flat so that the second edge 151 of the blade 140 can be engaged against a user's soft tissue surfaces for a more gentle feel.

Figure 4:
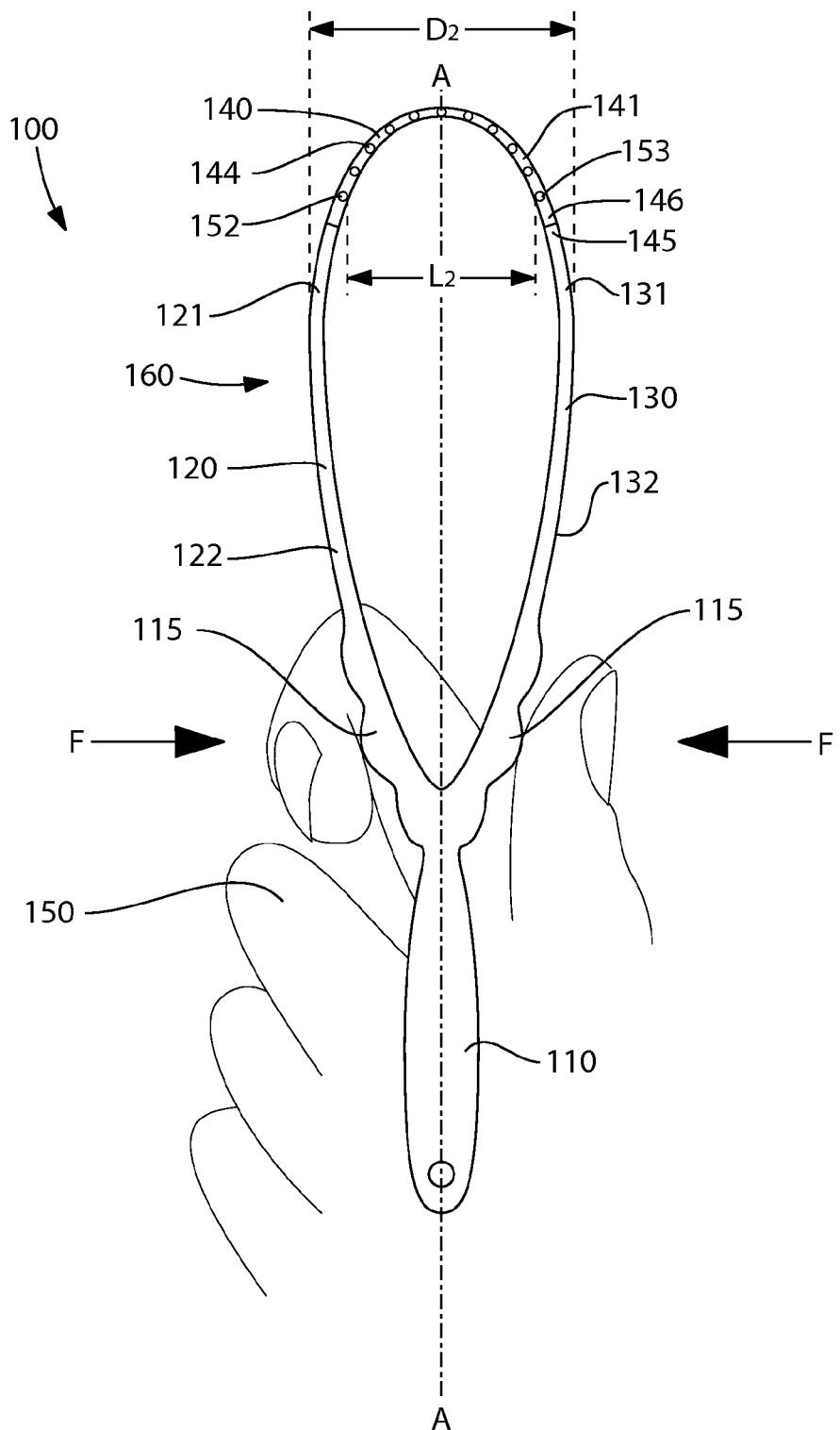
FIG. 4 is a front view of the tongue scraper of FIG. 1 in a flexed state.

Referring now to FIGS. 1 and 4 concurrently, the adjustability of the width of the oral care implement 100 will be discussed. FIG. 1 illustrates the oral care implement 100 in a normal state (i.e., a resting state in which no force is applied to the oral care implement 100 by the user). In other words, in FIG. 1 there are no external forces or pressures acting on either of the first and second prong members 120, 130, or elsewhere on the oral care implement 100, and the oral care implement 100 is in its natural pre-formed shape. In the normal state, there is a first distance $D_1$ between the outer surface 122 of the first prong member 120 and the outer surface 132 of the second prong member 130 at their respective distal ends 121, 131.

FIG. 4 illustrates the oral care implement 100 in a flexed state. The oral care implement 100 is adjusted from the normal state to the flexed state by applying an inward radial force F to the outer surfaces 122, 132 of the first and second prong members 120, 130, concurrently. This force F is applied by the user applying pressure to the finger grip protrusions 115. In the illustrated embodiment, the force F is created by a user's hand 150 squeezing the outer surfaces 122, 132 of the first and second prong members 120, 130 at the finger grip protrusions 115 in an inward direction as shown by the arrows. Of course, the invention is not so limited and the force F may be applied in other ways than by a user's hand and at other locations.

The force F is applied to the outer surfaces 122, 132 of the first and second prong members 120, 130 so as to have a component that is substantially perpendicular to the longitudinal axis A-A. In the fully flexed state illustrated in FIG. 4, there is a second distance $D_2$ between the outer surface 122 of the first prong member 120 and the outer surface 132 of the second prong member 130 at their respective distal ends 121, 131. The second distance $D_2$ is less than the first distance $D_1$, such that the first and second prong members 120, 130 are closer to each other in the flexed position than in the normal position.

FIG. 4 illustrates the oral care implement 100 in a fully flexed state. However, the oral care implement 100 may be flexed to less than the fully flexed state when desired. Specifically, the greater the force F that acts on the outer surfaces 122, 132 of the first and second prong members 120, 130, the closer together the first and second prong members 120, 130 will become. A lesser force F will move the first and second prong members 120, 130 together, but to a lesser extent. In other words, the second distance $D_2$ decreases as the force F increases.

As the force F is applied to the first and second prong members 120, 130, the distance between the distal ends 121, 131 of the first and second prong members 120, 130 changes from $D_1$ to $D_2$ (or any distance therebetween). As a result, the blade 140 bows and additional amount and extends further in the longitudinal direction away from the handle 110. As soon as the force F is terminated, the first and second prong members 120, 130 are biased back to the normal state illustrated in FIG. 1 by the resiliency of the blade 140. The first and second prong members 120, 130 remain in the normal state unless a force F is applied to the outer surfaces 122, 132 of the first and second prong members 120, 130. Furthermore, the first and second prong members 120, 130 automatically return to the normal state when the force F is no longer applied.

Due to the integral nature of the first and second prong members 120, 130 and the blade 140, when the distance between the first and second prong members 120, 130 decreases as a result of the force F, the curve/contour of the blade 140 increases, thereby decreasing the overall width occupied by the blade 140.

Stated another way, the first edge 141 of the blade 140 has a first transverse length $L_1$ measured as a straight (i.e., linear) line perpendicular to the longitudinal axis A-A between a left-most protuberance 152 and a right-most protuberance 153 when the first and second prong members 120, 130 are in the normal state. Furthermore, the first edge 141 of the blade 140 has a second transverse length $L_2$ measured as a straight (i.e., linear) line perpendicular to the longitudinal axis A-A between the left-most protuberance 152 and the right-most protuberance 153 when the first and second prong members 120, 130 are in the flexed state. The second length $L_2$ is less than the first length $L_1$. Thus, as the magnitude of the force F increases, the length of the first edge 141 of the blade 140 measured as a straight (i.e., linear) line perpendicular to the longitudinal axis A-A between the outermost protuberances 152, 153 decreases as a result of the curvature of the blade 140 increasing. This decrease in the length allows the blade 140 to fit within a smaller mouth as necessary.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

While a number of embodiments of the current invention have been described and illustrated in detail, various alternatives and modifications will become readily apparent to those skilled in the art without departing from the spirit and scope of the invention. As various changes could be made in the above methods, compositions and structures without departing from the scope of the invention, it is intended that all matter contained in this application, including all mechanisms and/or modes of interaction described above, shall be interpreted as illustrative only and not limiting in any way the scope of the appended claims.

What is claimed is:

1. An oral care implement comprising:
   a handle extending along a longitudinal axis;
   a first prong member and a second prong member extending from a distal end of the handle, each of the first and second prong members having a distal end;
   a blade for scraping soft tissue, the blade extending between the distal ends of the first and second prong members; and
   the blade integrally formed with the first and second prong members, the first and second prong members transitioning into the blade at the distal ends of the first and second prong members;
   wherein the blade comprises a base formed of a first material and a layer formed of a second material overlying at least a portion of the base, the first material having a hardness that is greater than a hardness of the second material; and
   wherein a plurality of protuberances protrude from a first edge of the blade, the protuberances being formed of the first material and protruding through the layer formed of the second material.

2. The oral care implement according to claim 1 wherein the first and second prong members diverge from the longitudinal axis with distance from the distal end of the handle.

3. The oral care implement according to claim 1 wherein the blade comprises a second edge, wherein the second edge is formed by the second material and the first material forms the first edge.

4. The oral care implement according to claim 1 wherein the first and second prong members are adjustable between (1) a normal state having a first distance between the distal ends of the first and second prong members; and (2) a flexed state having a second distance between the distal ends of the first and second prong members, wherein the second distance is less than the first distance.

5. The oral care implement according to claim 4 wherein the first and second prong members are biased into the normal state.

6. The oral care implement according to claim 4 wherein the first and second prong members are adjusted into the flexed state by applying a force to an outer surface of each of the first and second prong members, wherein the force is applied in a direction substantially perpendicular to the longitudinal axis.

7. The oral care implement according to claim 4 wherein a bow of the blade increases in a longitudinal direction away from the handle when the first and second prong members are moved from the normal state to the flexed state.

8. An oral care implement comprising:
   a handle extending along a longitudinal axis;
   a first prong member and a second prong member extending from a distal end of the handle, each of the first and second prong members having a distal end; and
   a blade for scraping soft tissue, the blade connected to and extending between the distal ends of the first and second prong members;
   wherein the blade comprises a base formed of a first material and a layer formed of a second material overlying at least a portion of the base, the first material having a hardness that is greater than a hardness of the second material, the second material being an elastomeric material; and further comprising a plurality of nubs for engaging soft tissue, wherein the nubs are column-like protrusions that extend from a first edge of the blade in a spaced-apart manner through the layer of the second material.

9. The oral care implement according to claim 8 wherein the first and second prong members diverge from the longitudinal axis with distance from the distal end of the handle.

10. The oral care implement according to claim 8 wherein the layer overlies a first portion of the base and leaves a second portion of the base uncovered.

11. The oral care implement according to claim 8 wherein the layer substantially surrounds the base.

12. The oral care implement according to claim 11 further comprising an aperture in the base, and wherein the layer extends through the aperture.

13. The oral care implement to claim 8 wherein the blade comprises a second edge, wherein the first edge is formed by the second material and the first material forms the second edge.

14. The oral care implement according to claim 8 wherein the blade is integrally formed with the first and second prong members, the first and second prong members transitioning into the blade at the distal ends of the first and second prong members.

15. The oral care implement according to claim 8 wherein the first and second prong members are adjustable between (1) a normal state having a first distance between the distal ends of the first and second prong members; and (2) a flexed state having a second distance between the distal ends of the first and second prong members, wherein the second distance is less than the first distance.

16. The oral care implement according to claim 15 wherein the first and second prong members are biased into the normal state.

17. The oral care implement according to claim 15 wherein the first and second prong members are adjusted into the flexed state by applying a force to an outer surface of each of the first and second prong members, wherein the force is applied in a direction substantially perpendicular to the longitudinal axis.

18. The oral care implement according to claim 15 wherein a bow of the blade increases in a longitudinal direction away from the handle when the first and second prong members are moved from the normal state to the flexed state.

19. An oral care implement comprising:
a handle extending along a longitudinal axis;
a first prong member and a second prong member extending from a distal end of the handle, each of the first and second prong members having a distal end; and
a blade for scraping soft tissue, the blade connected to and extending between the distal ends of the first and second prong members;
wherein the blade comprises a base formed of a first material and a layer formed of a second material overlying at least a portion of the base, the first material having a hardness that is greater than a hardness of the second material;
wherein the base comprises an aperture;
wherein the layer substantially surrounds the base and extends through the aperture; wherein the first material protrudes though the layer of the second material at a plurality of spaced apart locations.

* * * * *